US008849366B2

(12) United States Patent
Pfeiffer et al.

(10) Patent No.: US 8,849,366 B2
(45) Date of Patent: Sep. 30, 2014

(54) CATHETER SYSTEM HAVING AN OPTICAL PROBE AND METHOD FOR THE APPLICATION OF AN OPTICAL PROBE IN A CATHETER SYSTEM

(75) Inventors: Ulrich Pfeiffer, Munich (DE); Daniel Moulas, Bad Oeynhausen (DE); Reinhold Knoll, Munich (DE)

(73) Assignee: Up-Med GmbH, Munich (DE)

( * ) Notice: Subject to any disclaimer, the term of this patent is extended or adjusted under 35 U.S.C. 154(b) by 1138 days.

(21) Appl. No.: 12/671,619

(22) PCT Filed: Jul. 25, 2008

(86) PCT No.: PCT/EP2008/006137
§ 371 (c)(1),
(2), (4) Date: Feb. 3, 2011

(87) PCT Pub. No.: WO2009/015835
PCT Pub. Date: Feb. 5, 2009

(65) Prior Publication Data
US 2011/0118577 A1    May 19, 2011

(30) Foreign Application Priority Data

Jul. 31, 2007   (DE) .......................... 10 2007 035 847

(51) Int. Cl.
| | |
|---|---|
| *A61B 5/1455* | (2006.01) |
| *A61B 5/145* | (2006.01) |
| *A61B 5/00* | (2006.01) |
| *A61M 25/00* | (2006.01) |
| *A61B 5/1459* | (2006.01) |
| *A61M 25/01* | (2006.01) |
| *A61B 5/027* | (2006.01) |

(52) U.S. Cl.
CPC ......... *A61M 25/00* (2013.01); *A61M 2025/008* (2013.01); *A61M 25/0125* (2013.01); *A61B 5/14542* (2013.01); *A61B 5/412* (2013.01); *A61M 2025/0079* (2013.01); *A61B 5/1459* (2013.01); *A61B 5/027* (2013.01); *A61M 25/0021* (2013.01)
USPC .............................. 600/341; 600/342; 606/16

(58) Field of Classification Search
CPC ............. A61B 5/1455; A61B 5/14551; A61B 5/14552; A61B 5/14532; A61B 5/1459; A61B 5/0084; A61B 5/0086; A61B 1/07; A61B 1/00165; A61B 18/22; A61B 18/24; G02B 6/3825; G02B 6/3897
USPC ......... 600/310, 322, 341, 342, 327, 332, 182; 385/53, 88, 103; 606/16
See application file for complete search history.

(56) References Cited

U.S. PATENT DOCUMENTS

| | | | |
|---|---|---|---|
| 4,718,423 A | | 1/1988 | Willis et al. |
| 4,795,434 A | * | 1/1989 | Kujawski ...................... 600/342 |

(Continued)

FOREIGN PATENT DOCUMENTS

| | | |
|---|---|---|
| DE | 102006010457 A1 | 9/2007 |
| EP | 0891807 A2 | 1/1999 |

(Continued)

OTHER PUBLICATIONS

International Search Report dated Jul. 10, 2008 issued in connection with PCT/EP2008/006137.

*Primary Examiner* — Eric Winakur
(74) *Attorney, Agent, or Firm* — Leydig, Voit & Mayer, Ltd.

(57) ABSTRACT

A catheter system includes a flexible, elongated base body adapted to be applied to a vein central-venously and having a base distal end; a fiber-optic probe having a probe distal part; a fiber-optic lumen receiving the fiber-optic probe; and an attachment element configured to avoid a longitudinal displacement of the fiber-optic probe relative to the fiber-optic lumen and configured to detach so as to allow removal of the fiber-optic probe through the longitudinal displacement of the fiber-optic probe relative to the fiber-optic lumen. The attachment element has a connector piece firmly connected to the fiber-optic probe and a counter-piece firmly connected to the base body, wherein the connector piece is connectable to the counter-piece, the connector piece having a shaft piece adjustable lengthwise and disposed on the connector piece so as to vary a length of the connector piece.

11 Claims, 3 Drawing Sheets

(56) References Cited

U.S. PATENT DOCUMENTS

| | | |
|---|---|---|
| 5,634,720 A | 6/1997 | Gallup et al. |
| 5,673,694 A | 10/1997 | Rivers |
| 2004/0064021 A1 | 4/2004 | Pfeiffer |

FOREIGN PATENT DOCUMENTS

| | | |
|---|---|---|
| EP | 1402917 A2 | 3/2004 |
| JP | H 08 500 030 A | 1/1996 |
| JP | H 11 501 553 A | 2/1999 |
| JP | 2004 113 799 A | 4/2004 |
| JP | 2005 348 947 A | 12/2005 |
| WO | 8502101 A1 | 5/1985 |
| WO | 9705820 A1 | 2/1997 |
| WO | WO 01 91 661 A1 | 12/2001 |
| WO | 2007033318 A2 | 3/2007 |

* cited by examiner

CATHETER SYSTEM HAVING AN OPTICAL PROBE AND METHOD FOR THE APPLICATION OF AN OPTICAL PROBE IN A CATHETER SYSTEM

This application is a U.S. National Phase Application under 35 U.S.C. §371 of International Application No. PCT/EP2008/006137, filed on Jul. 25, 2008, and claims benefit to German Application No. DE 10 2007 035 847.6, filed on Jul. 31, 2007. The International Application was published in German on Feb. 5, 2009 as WO 2009/015835 under PCT Article 21 (2).

The invention relates to a catheter system having an optical probe and a method for the application of an optical probe in a catheter system. In particular, the invention relates to a catheter with fibre optics and a method for introducing the optical fibre into the catheter with an accurate fit.

BACKGROUND

In intensive care medicine, central venous catheters (CVCs) with several lumina, so-called multi-lumen CVCs, are frequently used. With these multi-lumen CVCs various parameters are ascertained, infusion solutions, blood and blood derivatives and pharmaceutical products are delivered via various lumina and blood samples taken for blood-gas analysis, haematological and biochemical tests. It is also known to introduce fibre-optic probes via a fibre-optic lumen in order for example to measure central venous oxygen saturation (Scv02).

A catheter with optical fibres is described in EP 1 402 917. The catheter system is suitable for the simultaneous, continuous, reciprocally uninfluenced measurement of central-venous oxygen saturation. It has a central venous catheter with a fibre-optic lumen and a fibre-optic probe which can be introduced into the fibre-optic lumen in order to take reflective oximetry measurements. To avoid a longitudinal displacement of the fibre-optic probe relative to the fibre-optic lumen a connector piece firmly connected to the fibre-optic probe and a counter-piece firmly connected to the catheter are provided which can be connected to one another.

Because of the fixedly prefabricated length of the fibre-optic probe and the firm connection of the fibre-optic probe to the connector piece, a precise matching of the individual fibre-optic probe to the central venous catheter to be used is necessary. In order to measure the central venous oxygen saturation via the probe, the tip of the probe projects beyond the distal end of the CVC by approximately 25 mm±5 mm It is thereby ensured that central venous blood flows round the probe and a measurement at this point gives the central venous oxygen saturation. Simultaneously, the tip of the probe must not lie in the right atrium, where it would lead to irritations of the heart.

Because of the different length of individual CVCs from different manufacturers it is therefore necessary to provide fibre-optic probes cut to different lengths for the very wide range of applications, which are matched to the respective CVC in terms of the length such that these criteria are met. If a fibre-optic probe which is too short is used by mistake, the correct value of the central venous oxygen saturation cannot be ascertained, as the tip of the probe is then still in the CVC. If a fibre-optic probe which is too long is chosen, there is a risk that the probe will come to rest in the right atrium, leading to irritations of the heart or the death of the patient. A probe which projects too far from the CVC is possibly not adequately guided and can then easily be unfavourably positioned, e.g. rest against the vascular wall or bend.

SUMMARY OF THE INVENTION

An aspect of the present was therefore to provide a catheter system with in particular a fibre-optic probe in which the disadvantages of the state of the art are avoided.

In an embodiment, a catheter system has a flexible, elongated base body (2) that can be applied central-venously, a fibre-optic probe (8), a fibre-optic lumen for receiving the fibre-optic probe (8), and an attachment means (25) for avoiding a longitudinal displacement of the fibre-optic probe (8) relative to the fibre-optic lumen, wherein the attachment means (25) can be detached in order to allow a longitudinal displacement of the fibre-optic probe (8) relative to the fibre-optic lumen for removing the optical probe (8), wherein the attachment means (25) has a connector piece (7) that is firmly connected to the fibre-optic probe (8) and a counter-piece (6) that is firmly connected to the base body (2), that can be applied central-venously, which may be connected to each other, and wherein the distance between the distal end (3) of the central-venously applicable base body (2) and the distal end (14) of the fibre-optic probe (8) is adjusted to a predetermined value in the connected state by the firm connections between the fibre-optic probe (8) and the connector piece (7) as well as the base body (2) and the counter-piece (6), wherein additionally a shaft piece (30) that is adjustable with regard to the length thereof is provided on the connector piece (7), via which the length of the connector piece (7) and thus the length of the fibre-optic lumen may be varied.

A catheter system is a system consisting of various components for measuring a patient's parameters, applying various substances, taking samples or introducing measuring probes. Central venous catheters with several lumina, so-called multi-lumen CVCs, are particularly preferred. These catheters are introduced into the central venous system and remain there. The operator can introduce probes via preferably several connections in the non-sterile area, remove blood, administer pharmaceutical products, etc., via adaptors.

The catheter system has in particular a base body which is preferably flexible. This base body can be applied central-venously, i.e., can be introduced into the central venous system and remains there. The base body is then preferably connected to an adaptor which has at least one connector piece, preferably three connector pieces, via which then probes or other systems can then be connected.

The catheter system has at least one fibre-optic probe, via which for example the central venous oxygen saturation can be continuously measured via optical measurement methods, in particular by means of fibre-optic reflection oximetry. Particularly preferably the fibre-optic probe has a coating, in particular a thin, flexible outer shaft, consisting of bio- and haemocompatible material, such as e.g. polyurethane. The optical fibre, which preferably consists of flexible plastic fibres, is then housed in this.

At least one fibre-optic lumen is provided in the catheter system, i.e. a continuous area in which the fibre-optic probe can be introduced and can be pushed through to the distal end of the base body. This fibre-optic lumen thus extends, via the connector pieces, an adaptor, to the base body. Particularly preferably, in addition to the fibre-optic lumen, further lumina are also provided, particularly preferably a total of 4 lumina, in particular 5 lumina.

The attachment means are provided in order to connect the fibre-optic probe introduced into the catheter system firmly to the catheter system, in particular to the adaptor of the catheter system. In this way a longitudinal displacement of the fibre-optic probe relative to the fibre-optic lumen is avoided. Such an attachment means can preferably be a Luer-Lock connection. The attachment means are thereby suitable to fix the fibre-optic probe in the desired position and these attachment means can then be detached again in order to remove the fibre-optic probe from the catheter system.

The attachment means preferably have a connector piece firmly connected to the fibre-optic probe. This connector piece is firmly connected to the probe, with the result that a displacement of the probe relative to the connector piece is not possible. As counter-piece to this connector piece the attachment means preferably have a counter-piece firmly connected to the base body that can be applied central-venously. This counter-piece can for example be attached to an adaptor between the base body and the actual counter-piece. Preferably, the fibre-optic lumen extends through this counter-piece to the distal end of the flexible base body. The connector piece and the counter-piece can be connected to one another, particularly preferably by a Luer-Lock and the distance between the distal end of the base body that can be applied central-venously on the one hand and the distal end of the fibre-optic probe when introduced on the other is thereby fixed.

According to the present invention a shaft piece, adjustable with regard to the length is preferably provided which is particularly preferably formed at the connector piece. The length of the connector piece can thus be varied or set via the shaft piece which can be set with regard to the length. The length of the fibre-optic lumen can thus be varied by the shaft piece which can be adjusted with regard to the length. Because the fibre-optic probe is firmly connected to the connector piece, the shaft piece adjustable with regard to the length causes the probe to be displaceable inside the fibre-optic lumen by the length by which the shaft piece adjustable with regard to the length can be varied. In this way it is possible, via the shaft piece adjustable with regard to the length, to use fibre-optic probes of different lengths for an applied CVC, the projecting length of the fibre-optic probe relative to the predetermined CVC being optimally adjustable preferably before applying the probe, via the shaft piece adjustable with regard to the length. A standard fibre-optic probe, the length of which is then adjusted to fit the corresponding CVC, via the shaft piece, adjustable with regard to the length, can thus be used for a very wide range of CVCs customary in the trade.

Preferably, the intensity of the reflected optical radiation can additionally be measured and the plausibility of the obtained oxygen-saturation value checked during the introduction of the optical fibre with the connected evaluation apparatus for the measurement of the oxygen saturation. When the tip of the probe enters the free bloodstream a change in the optical intensity of the registered signal can be established and the measured value is preferably monitored to ensure that it lies in the plausible range. Once the evaluation apparatus has established this, a signal for the correct placement of the probe is sent to the operator.

In a further advantageous embodiment example of the present invention the shaft piece adjustable with regard to the length (30) has a tube section (35) which is formed displaceable in the direction of the fibre-optic lumen in an inner space (36) of the connector piece (7).

By providing a tube section or cylindrical section on the one side and a matching inner space of the connector piece or external cylinder on the other, these two elements can be displaced towards each other and thus offer, in the manner of a telescope, a corresponding extension possibility for the connector piece, to the proximal end of which the fibre-optic probe is firmly connected. For example, by telescoping two matched cylinders one inside the other the shaft piece adjustable with regard to the length and thus the connector piece can be lengthened or shortened. In this way, the length of the fibre-optic probe projecting from the connector piece or the shaft piece adjustable with regard to the length can also be shortened or lengthened. Particularly preferably, adjustable areas of up to 50 mm, preferably 20 to 40 mm, particularly preferably 30 mm maximum extension can be achieved through the shaft piece adjustable with regard to the length.

In a further advantageous embodiment example of the present invention the tube section (35) has at its distal end a sealing lip (38) via which the tube section (35) can be sealed off vis-à-vis the inner space (36) of the connector piece (7).

A sealing lip can be provided between the two parts to be moved towards each other, in order to increase tightness. Particularly preferably, plastics, silicons, etc., which satisfy medical requirements as regards toxicity and sterility are used for this. Particularly preferably the sealing lip is provided at the preferably cylindrical tube section at the distal end, with the result that the sealing lip comes to rest against the inner surface of the connector piece or of the shaft piece, adjustable with regard to the length, and seals off this area.

In a further advantageous embodiment example of the present invention the shaft piece adjustable with regard to the length (30) has at least one length mark (26).

Through the provision of a length mark on the shaft piece adjustable with regard to the length shaft piece it is easily possible for the operator to set the length which in the case of the present fibre-optic probe and the applied CVC ensures the correct projection of the distal end of the fibre-optic probe over the distal end of the base body of the CVC. These length marks can particularly preferably be coloured and also correspond to a colour coding of the CVC.

In a further advantageous embodiment example of the present invention a locking device (27) is provided for fixing the shaft piece (30), adjustable with regard to the length.

Through the provision of a locking device it is possible to lock the shaft piece adjustable with regard to the length in this position or in this length setting after setting the desired difference in length. Such a locking device can for example be a developed slot and lug which mesh in special positions and lock the shaft piece adjustable with regard to the length at this point. The locking device can particularly preferably be arranged in the non-sterile area, i.e. on the outer surface of the connector piece or of the shaft piece adjustable with regard to the length. Particularly preferably, screw closures which ensure locking by screwing are also provided here. Particularly preferably a raster grid lying in the unsterile area is provided.

In a further advantageous embodiment example of the present invention the fibre-optic probe (8) has a balloon (28) at its distal end.

Preferably at least one fibre-optic probe has at its distal end a small balloon to be filled, with gas if necessary, preferably $CO_2$, or with a fluid, preferably with common salt solution. Through this balloon the tip of the probe can be washed with the bloodstream into the right ventricle of the heart, where it is to remain. In this way it is possible, through such a float or resistor to wash the distal tip of the fibre-optic probe 10 to 15 cm into the right ventricle of the heart and there measure the effectively mixed-venous oxygen saturation in the right ventricle of the heart. The balloon can preferably remain inflated in order that the distal end of the probe remains with the balloon through the bloodstream in the right ventricle of the heart.

Preferably, the balloon fibre-optic probe can alternatively also have, at the tip proximally behind the balloon, a thermistor to conduct the thermodilution measurements; the thermal indicator is preferably injected into the superior vena cava via a free lumen of the multi-lumen CVC. In addition it is also possible that the balloon fibre-optic probe has a pressure lumen opening proximally behind the balloon, via which the pressure in the right ventricle of the heart can be continuously measured by means of a liquid column.

Alternatively the pressure in the right ventricle of the heart can also be measured via the balloon of the fibre-optic probe. For this, the balloon is particularly preferably filled with liquid, preferably common salt solution. Here, the pressure required to expand the balloon is added to the intravasal pressure acting from outside in the right ventricle of the heart. By electronically tracking the pressure pattern when filling the balloon the filling pressure can be eliminated after reaching the desired balloon-filling state and the pure intravasal pressure in the right ventricle of the heart ascertained or displayed. It is advantageous if the balloon has a high volume/filling pressure ratio.

In an embodiment example of the present invention a balloon of the above-described type can preferably also be attached to a probe other than the fibre-optic probe described here, either another fibre-optic probe in another catheter system or another functional probe. According to the invention the balloon probe can also be used with catheter systems other than that described here.

A catheter system is particularly preferably provided in which two optical fibres are contained, one of which is provided firmly integrated in a multi-lumen catheter for measuring the oxygen saturation in the superior vena cava and the alternative probe with a balloon for measuring the mixed-venous oxygen saturation.

In a further advantageous embodiment example of the present invention the fibre-optic probe (8) comprises more than one optical fibre.

According to a further feature of the invention the fibre-optic probe comprises more than one optical fibre which can be applied through the same fibre-optic lumen. A further measurement can be carried out through a second optical fibre. This can take place as a control measurement in roughly the same area or at another location by providing a different length of the second optical fibre. Particularly preferably the catheter system has a further fibre-optic lumen through which a further fibre-optic probe can be introduced into the CVC. Thus it is possible, for example, that the first fibre-optic probe lies in the superior vena cava, where it measures the oxygen saturation in the superior vena cava (ScsO2), while a further probe comes to rest in the right ventricle of the heart and measures the oxygen saturation in the right ventricle of the heart (SmvO2). By measuring these two parameters the oxygen saturation in the inferior vena cava (SciO2) can then preferably also be estimated. This takes place preferably according to the following formula:

$$SmvO2=(BFci \times SciO2+BFcs \times ScsO2)/CO$$

wherein
BFci=Blood flow in the inferior vena cava
BFcs=Blood flow in the superior vena cava
SciO2=Oxygen saturation in the inferior vena cava
ScsO2=Oxygen saturation in the superior vena cava
SmvO2=Mixed-venous oxygen saturation in the right ventricle of the heart
CO=Cardiac output=BFci+BFcs To obtain a sufficiently accurate estimate, BFci is assumed to be 65% CO, BFcs 35% CO. This can preferably be input by the user.
Consequently:

$$SmvO2=0.65SciO2+0.35ScsO2$$

or $$SciO2=(SmvO2-0.35ScsO2)/0.65$$

Through this catheter system it is possible that, for use with different CVCs, one or few probes of different lengths must be produced and held ready. Furthermore, through the placing of alternative probes with the balloon in the right ventricle of the heart, it is possible to measure effectively mixed-venous blood. In the case of the conventional catheter systems with one probe in which only one tip lies in the superior vena cava, the oxygen saturation is also measured only in the superior vena cava. But in the case of several states of shock such as with sepsis, the oxygen saturations in the superior and inferior vena cava differ substantially from each other. It is often clearly lower in the inferior vena cava. Of substantially greater clinical interest, therefore, is the mixed-venous oxygen saturation in the right ventricle of the heart which can be measured by the present catheter system with two fibre-optic probes. The presence of different oxygen saturation values SciO2 and SmvO2 can be used indicating a correct positioning and an alert can preferably be issued if the values are implausible.

In an embodiment, a method for the application of a fibre-optic probe (8) in a catheter system (1) comprises the steps of:
Introducing a fibre-optic probe (8) into a connector piece (7),
Setting a shaft piece (30) adjustable with regard to the length to a predetermined length for the accurately-fitting positioning of the fibre-optic probe (8) in the catheter system (1),
Fixing the fibre-optic probe (8) relative to the connector piece (7).

It is possible through the method according to the invention to use a few different lengths of probes and, via the shaft piece adjustable with regard to the length, pre-set the corresponding length to the suitable CVC before the fibre-optic probe is then introduced into the catheter system and is fixed relative to the connector piece and thus inside the fibre-optic lumen.

In a further advantageous embodiment example of the present invention the step is additionally provided:
Locking the shaft piece (30) adjustable with regard to the length at a predetermined length.

By locking the shaft piece adjustable with regard to the length after setting the length which the specifically applied CVC requires, this length cannot be changed by mistake during further handling and thus the distal tip of the fibre-optic probe is fixed vis-à-vis the distal end of the base body of the CVC.

When using a probe with balloon the distal end with the balloon can be placed where the operator considers desirable by varying the length via the corresponding shaft piece.

In a further embodiment example a method is provided which further comprises the step of:
Measuring an intensity of the reflected optical radiation in the fibre-optic probe (8) during the introduction of the optical fibre with the connected evaluation apparatus for measurement of the oxygen saturation; checking the plausibility of the measured intensity values.

Preferably, the intensity of the reflected optical radiation can thus be measured and the plausibility of the obtained oxygen-saturation value checked during the introduction of the optical fibre with the connected evaluation apparatus for the measurement of the oxygen saturation. When the probe tip enters the free bloodstream, an amendment of the optical intensity of the registered signal can be established and the measurement value is preferably checked whether it lies in the plausible range. Once the evaluation apparatus has established this, a signal for the correct placement of the probe is sent to the operator.

In a further embodiment example a method is provided which further comprises the step of: Emitting a signal if the fibre-optic probe (8) is placed correctly.

Displays on a monitor, acoustic signals, visual signals, etc., can be used as a signal. The correct placing results preferably from the plausibility of the measured values. If such a plausible range is achieved when advancing the probe a signal is emitted which shows the correct placement of the fibre-optic probe.

BRIEF DESCRIPTION OF THE FIGURES

An embodiment example of the present invention is described in the Figures. There are shown in.

DETAILED DESCRIPTION

Figure 1:
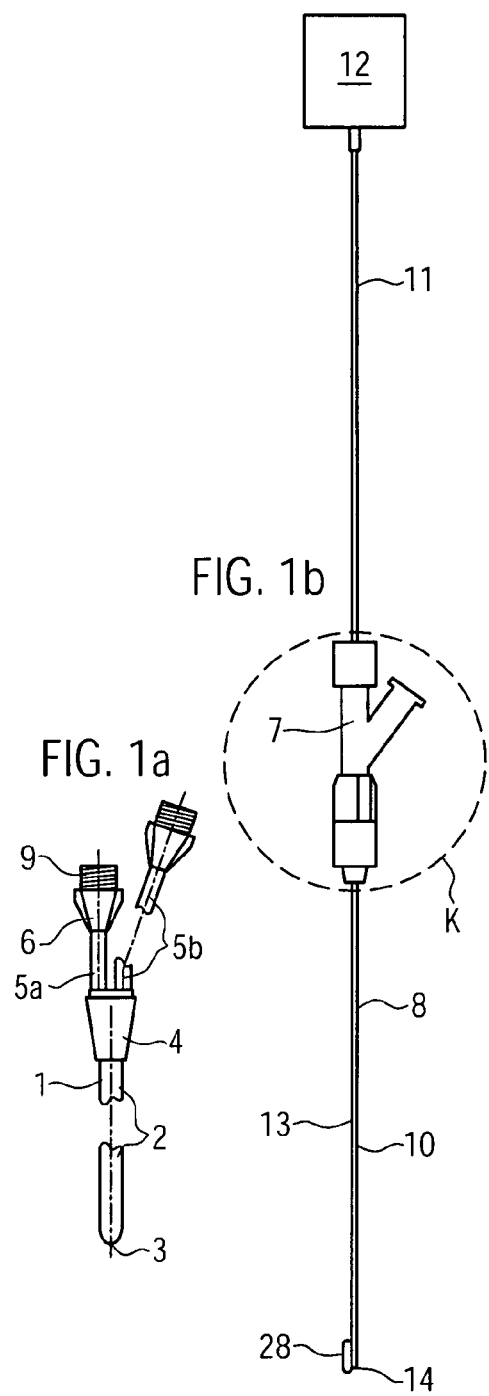
FIG. 1a a partial view, interrupted more than once, of a central venous multi-lumen catheter which is part of a catheter system according to the invention.
FIG. 1b a view of a fibre-optic probe according to the invention.

In FIG. 1a a central-venous multi-lumen catheter 1 is shown which has a flexible, elongated base body 2, shown interrupted that can be applied central-venously in which several lumina are formed, the distal openings (not shown) of which are arranged at the distal end 3 of the base body 2 or in the vicinity of the distal end 3 of the base body 2. Proximally, the lumina run above a fork 4 in several continuations 5A, 5B, wherein continuation 5B is shown interrupted. The fibre-optic lumen (not visible), which has a clearly greater diameter than the outer diameter of the distal part 10 of the fibre-optic probe 8, runs from the distal end 3 of the catheter base body 2 through same and on through the continuation 5A to a counter-piece 6 for the connector piece 7 of the fibre-optic probe 8. The counter-piece 6 is firmly connected to the base body 2 via the continuation 5A and the fork 4. The counter-piece 6 has an external thread 9 via which the connector piece 7 can be connected in positive fit after introducing the distal part of the fibre-optic probe into the fibre-optic lumen. Fibre-optic probes can be introduced into the catheter system via the continuation 5A in exactly the same way as via the continuation 5B.

In FIG. 1b a fibre-optic probe 8 is shown which is suitable for measuring the central venous oxygen saturation. For this, it is connected, via an optical fibre running proximally into a cable 11, to a light source and measuring device 12 which is formed for the simultaneous emission and measurement of radiation and preferably has an evaluation unit. Seen distally from the connector piece 7, the optical fibres run in a thin, flexible shaft 13 which is provided with an antithrombogenic cover in the vicinity of its rounded distal end 14. The length of the distal end 10 is matched to the length of the fibre-optic lumen of the multi-lumen catheter 1 by adjusting the shaft piece, adjustable with regard to the length, of the connector piece 7. The connector piece 7 is firmly glued to the fibre-optic probe 8. At the distal end 14 of the fibre-optic probe 8 a balloon 28 is provided which if necessary can be filled with gas.

The fibre-optic probe 8 from FIG. 1b is then, in use, introduced into the catheter via for example the continuation 5A and thus into the base body 2. This continuation is connected firmly to the connector piece 7 by a Luer-Lock via the counter-piece 6 and the external thread 9.

Figure 2:
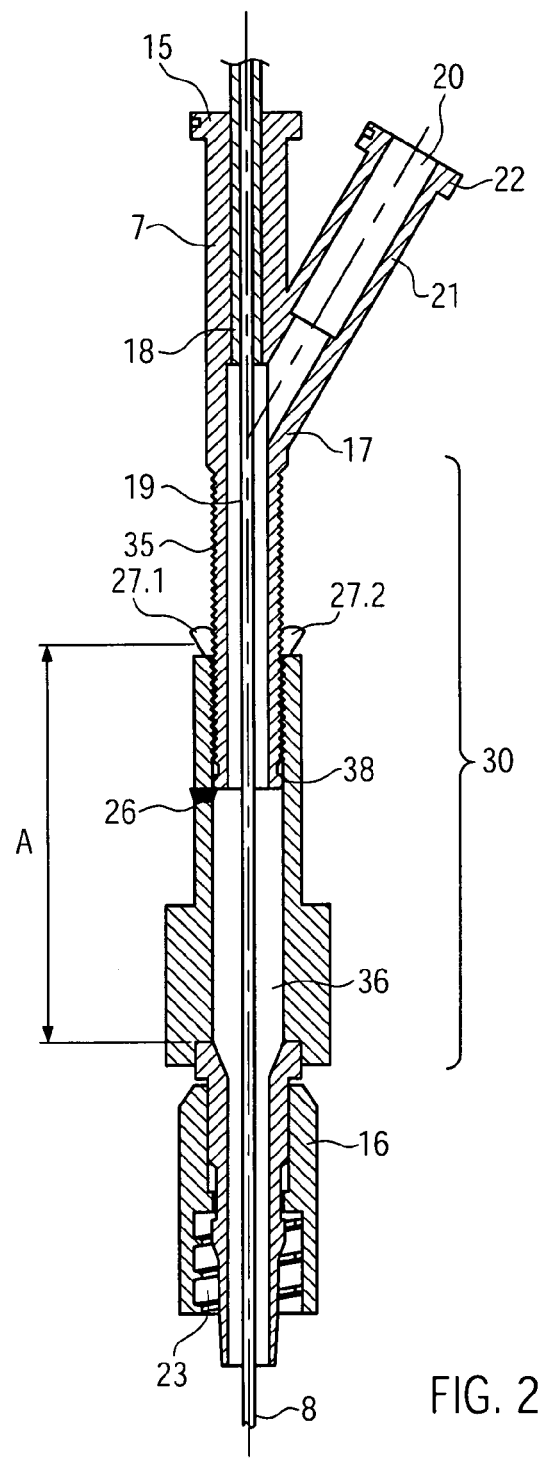
FIG. 2 a partial view in cross-section indicated in FIG. 1b by means of the dotted circle K, which essentially shows the connector piece with shaft piece adjustable with regard to the length and FIG. 3 a schematic view of the distal end of the base body of a multi-lumen catheter with the fibre-optic probes projecting therefrom according to an embodiment example of the present invention.

In FIG. 2 the connector piece 7 is shown in cross-section with the shaft piece 30 adjustable with regard to the length. The connector piece 7 consists of three parts 17, 18 and 19 glued to one another. The fibre-optic probe (8) is firmly glued to the closure part 15. An adjustable connection to the part 16 is created via a formed sleeve 35 The sleeve 35 can be moved back and forth in the provided cylindrical inner space 36 along the drawn-in two-way arrow A. As the fibre-optic probe 8 is firmly glued to the part 18 or the closure part 15, the fibre-optic probe is displaced forwards and backwards by the displacement of the sleeve 35 in the cylindrical inner space 36 inside the fibre-optic lumen. Thus the distal end of the fibre-optic lumen is varied by a displacement along the two-way arrow A relative to the distal end of the base body 2 of the catheter 1 in its projection over this end. In this way it is possible to precisely set the distal end of the fibre-optic probe 8 relative to the length of the base body 2 of the catheter 1. A length mark 26 is provided on the base body 16. The sleeve 35 has been advanced as far as this length mark 26 in the Figure. The sleeve 35 is held via the locking devices 27.1 and 27.2 in the cylindrical inner space 36 precisely at this point which is defined with the length mark 26. In this way the pre-chosen lock and the shaft piece 30 adjustable with regard to the length of the connector piece 7 can be set at a length of the fibre-optic probe 8 matched to the central venous catheter 1 used. A sealing lip 38 is provided in order to increase tightness.

Figure 3:
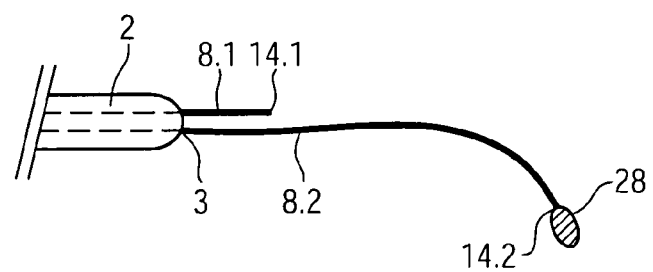

In FIG. 3 the distal end of the base body 2 of a catheter is shown schematically. Two fibre-optic probes 8.1 and 8.2 project at the distal end 3 of the base body 2. The distal end of the first fibre-optic probe 14.1 lies approximately 25 mm behind the distal end 3 of the base body 2. The distal end 14.2 of the fibre-optic probe 8.2 lies approximately 15 cm behind the distal end 3 of the base body 2. At the distal end 14.2 of the fibre-optic probe 8.2 a balloon 28 is shown which is inflated. In this way the fibre-optic probe 8.2 is stabilized in this position by the bloodstream and can be washed into the right ventricle of the heart and stabilized there. Effectively mixed-venous blood can then be measured there.

LIST OF REFERENCE NUMBERS

1 Multi-lumen catheter/catheter system
2 Base body
3 Distal end of the base body 2
4 Fork
5 Continuation
6 Counter-piece for connector piece 7
7 Connector piece
8 Fibre-optic probe
9 External thread
10 Distal part of the fibre-optic probe 10
11 Cable
12 Light source and measuring device 13 Flexible shaft
14 Distal end of the fibre-optic probe 8
15 Closure part
16 Threaded part
17 Y-part of the connector piece 7
18 Glued part
19 Interior of the Y-part 17
20 Flushing duct
21 Flushing pipe
22 Flange
23 Internal thread of the threaded part 16
25 Attachment means
26 Length mark
27 Locking device
28 Balloon
30 Shaft piece adjustable with regard to the length of the connector piece 7
35 Stroke/Piston/Plunger
36 Inner space of the cylinder
38 Sealing lip

The invention claimed is:

1. A catheter system comprising:
a fibre-optic probe having a probe distal part;
a flexible, elongated base body adapted to be applied to a vein central-venously and having a base distal end, the base body including a lumen that receives the fibre-optic probe;
and
an attachment element including a connector piece firmly connected to the fibre-optic probe and a counter-piece firmly connected to the base body, the connector piece being detachably connectable to the counter-piece so as to attach the fibre-optic probe with respect to the base body and provide removability of the fibre-optic probe from the base body by longitudinal displacement of the fibre-optic probe relative to the lumen when the connector piece and counter-piece are detached, the connector piece having a shaft piece that is adjustable in length so as to vary a length of the connector piece,
wherein a distance between the distal end of the base body and the distal end of the fibre-optic probe is adjustable to a predetermined value in a connected state of the attachment element by the connection between the fibre-optic probe and the connector piece and the connection between the base body and the counter-piece.

2. The system as recited in claim 1, wherein the shaft piece includes a tube section displaceable in a direction of the fibre-optic lumen in an inner space of the connector piece.

3. The system as recited in claim 2, wherein the tube section includes a sealing lip disposed at a distal end of the tube section, and wherein the tube section is sealed off via the sealing lip at the inner space.

4. The system as recited in claim 1, wherein the shaft piece includes at least one length mark.

5. The system as recited in claim 1, wherein the connector piece includes a locking device configured to fix the shaft piece.

6. The system as recited in claim 1, wherein the fibre-optic probe includes a balloon disposed at the distal end.

7. The system as recited in claim 1, wherein the fibre-optic probe includes more than one optical fibre.

8. A method for an application of a fibre-optic probe in a catheter system comprising:
introducing a fibre-optic probe into a connector piece that has a shaft piece with an adjustable length;
setting the shaft piece to a predetermined length so as to accurately position a distal end of the fibre-optic probe with respect to the connector piece; and
fixing the fibre-optic probe with reference to the connector piece.

9. The method as recited in claim 8, further comprising locking the shaft piece at the predetermined length.

10. The method as recited in claim 8, further comprising measuring an intensity of reflected optical radiation in the fibre-optic probe during a measuring of oxygen saturation using the optical-fibre probe and a connected evaluation apparatus, and checking a plausibility of measured intensity values.

11. The method as recited in claim 10, further comprising emitting a signal if the fibre-optic probe is correctly placed.

* * * * *